United States Patent [19]
Dewey

[11] Patent Number: 5,336,216
[45] Date of Patent: Aug. 9, 1994

[54] APPARATUS FOR DELIVERING A DEFOCUSED LASER BEAM HAVING A SHARP-EDGED CROSS-SECTION

[75] Inventor: David A. Dewey, Sunnyvale, Calif.

[73] Assignee: Coherent, Inc., Santa Clara, Calif.

[21] Appl. No.: 97,867

[22] Filed: Jul. 27, 1993

Related U.S. Application Data

[63] Continuation of Ser. No. 775,696, Oct. 10, 1991.

[51] Int. Cl.$^5$ .............................. A61B 1/06; F21V 7/04
[52] U.S. Cl. .............................................. 606/4; 5/11; 5/17; 359/379; 359/676; 359/809
[58] Field of Search ................. 128/395; 606/4, 5, 6, 606/7, 8, 9, 10, 11, 14, 17; 359/379, 380, 432, 434, 676, 691, 794, 809

[56] References Cited

U.S. PATENT DOCUMENTS

| | | | |
|---|---|---|---|
| 3,720,213 | 3/1973 | Hobart et al. | 128/395 |
| 4,576,160 | 3/1986 | Tanaka | 606/10 |
| 4,628,416 | 12/1986 | Dewey | 606/4 |
| 4,776,335 | 10/1988 | Nakanishi et al. | 128/395 |

FOREIGN PATENT DOCUMENTS

0492778A1  7/1992  European Pat. Off. ........ A61F 9/00

OTHER PUBLICATIONS

David A. Dewey, "Corneal and Retinal Energy Density with Various Laser Beam Delivery Systems and Contact Lenses," SPIE, vol. 1423, Ophthalmic Technologies, 1991, 25 pages.

Primary Examiner—Stephen C. Pellegrino
Assistant Examiner—Sonya C. Harris
Attorney, Agent, or Firm—Limbach & Limbach

[57] ABSTRACT

An apparatus for delivering a defocused laser beam to a sharp-edged spot (having variable size) in a target plane. The beam has a low power density in a plane of interest between the delivery apparatus and the target plane. In a preferred embodiment, the target plane is the retina of a patient's eye, and the defocused beam profile is controlled so that the beam has low power density at the eye's cornea. The beam produced by the invention is useful not only for ophthalmic surgery, but also for industrial laser heat treating and cutting applications in which a sharp-edged beam cross-section is needed at a target, particularly where delivery of low beam power densities at non-target structures are desirable. In a preferred embodiment of the inventive apparatus, an input laser beam emerges from an optical fiber, and a first lens (having short focal length) is mounted adjacent the optical fiber's output end to receive and transform the input beam. A second lens (having short focal length) is mounted with variable position between the first lens and the treatment site, for magnifying the image of the fiber core. Preferably, a lens system having long focal length (such as a pair of long focal length lenses) is mounted between the second lens and the target plane for relaying the magnified image of the fiber core to the target plane. By varying the position of the second lens and relay lens system, the characteristics of the beam delivered to the treatment site can be controlled.

13 Claims, 6 Drawing Sheets

FIG. 9
SHARP EDGED DEFOCUS, BEAM PROFILES AT THE 500μm SPOT SIZE

FIG. 10
STANDARD DEFOCUS, BEAM PROFILES AT THE 500μm SPOT SIZE

FIG. 12
OPHTHALMIC VERSION

FIG. 13
SURGICAL VERSION

APPARATUS FOR DELIVERING A DEFOCUSED LASER BEAM HAVING A SHARP-EDGED CROSS-SECTION

This application is a continuation of Ser. No. 07/775,696 filed Oct. 10, 1991.

FIELD OF THE INVENTION

The invention pertains to apparatus for delivering a defocused laser beam to a sharp-edged spot, for applications such as ophthalmic surgery. More particularly, the invention pertains to apparatus for delivering a defocused laser beam to a sharp-edged spot (having variable size) in a target plane, where the defocused beam profile is such that the beam delivers low power to a plane of interest between the delivery apparatus and the target plane.

BACKGROUND OF THE INVENTION

Figures 1A, 1B, 2, 3:
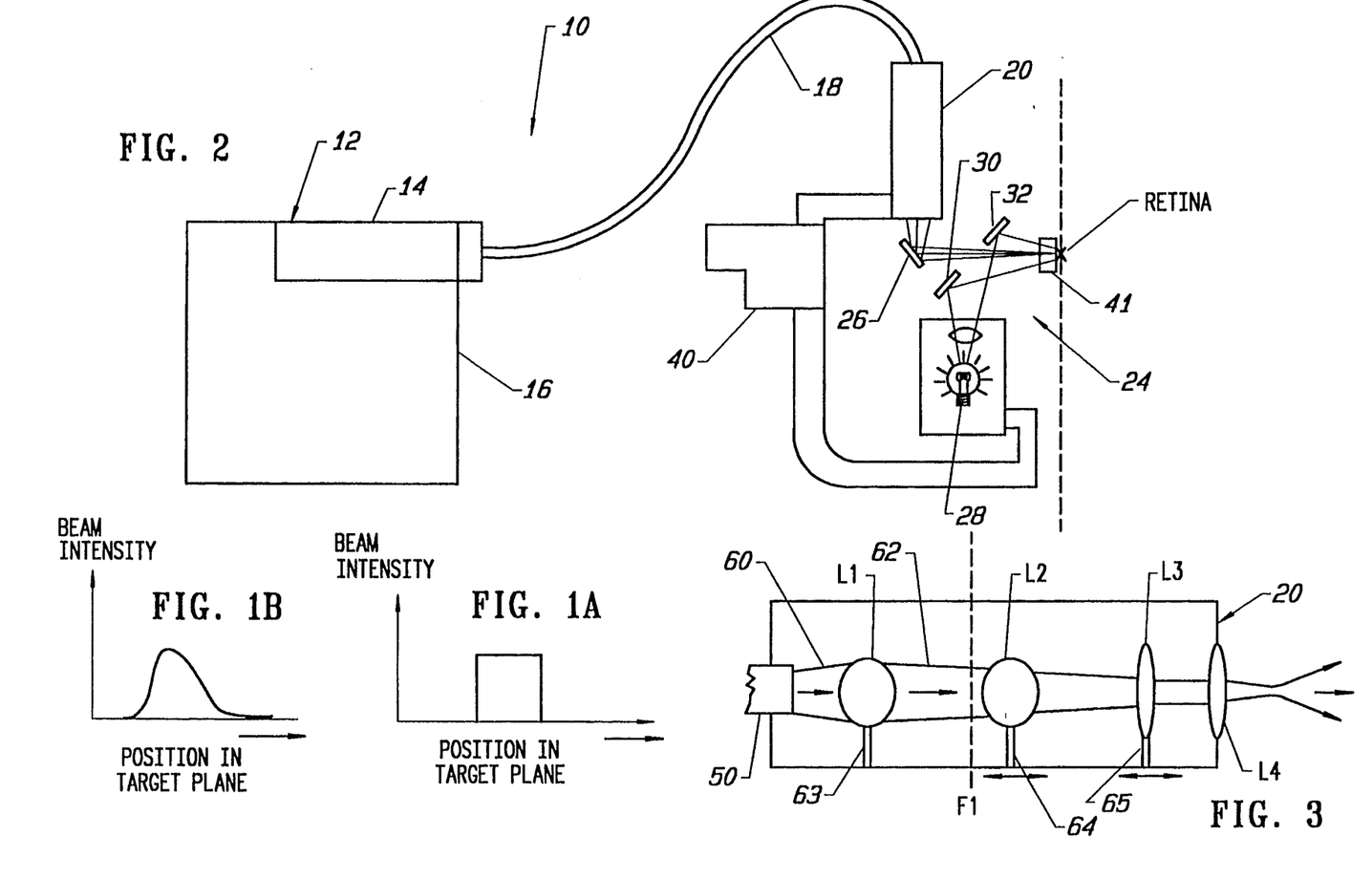
FIG. 1(a) is a graph of the intensity of a sharp-edged laser beam, versus position along a line in the plane of the beam's cross-section.
FIG. 1(b) is a graph of the intensity of a Gaussian laser beam, versus position along a line in the plane of the beam's cross-section.
FIG. 2 is a schematic diagram of an ophthalmic laser beam delivery system in which the invention can be embodied.
FIG. 3 is a side cross-sectional view of a preferred embodiment of the inventive apparatus.

Throughout this specification, the phrase "top hat" cross-section will be used to denote a laser beam cross-section having a sharply defined edge at a target plane. A graph of the intensity of a beam having a top-hat cross-section, versus position along a line in the target plane, will have a sharp-edged appearance as shown in FIG. 1(a). In contrast, the graph of the intensity of a beam having a Gaussian cross-section, versus position along a line in a target plane, will have a bell-shaped ("Gaussian") appearance as shown in FIG. 1(b).

Throughout this specification, the phrase "defocused" beam profile will be used to denote a beam profile in which the beam waist (i.e., the location along the beam profile at which the beam has its smallest cross-section) does not coincide with the target plane.

Ophthalmic laser beam delivery systems are designed to deliver a laser beam to a treatment site in a patient's eye (for example, to a desired location on the retina at which photocoagulation is to be performed). Typically, visible radiation also illuminates the treatment site to enable the physician to view a magnified image of the site. In a class of ophthalmic laser beam delivery systems in widespread use, both the treatment beam and a separate illuminating beam are directed along a common path through a microscope assembly (known as a "slit lamp") to the patient's eye.

Throughout the present specification, in the context of ophthalmic surgery, the phrase "target plane" will denote a plane through a treatment site in a patient's eye.

Figure 11:
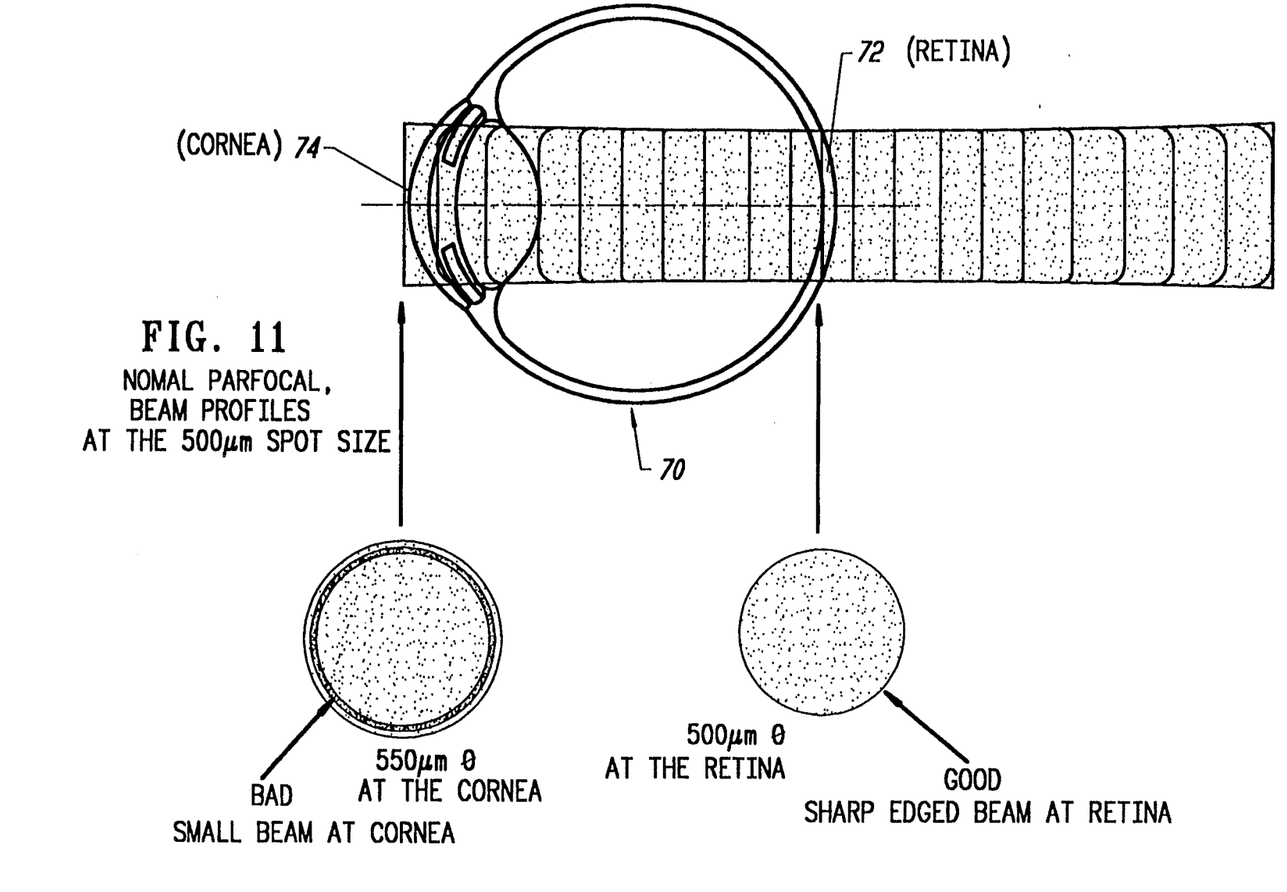
FIG. 11 is a diagram representing the profile of a beam delivered to a patient's eye by a conventional parfocal beam apparatus, and three different cross-sectional views of the beam in different cross-sectional planes along the beam profile.

Two types of conventional ophthalmic beam delivery systems, each of which delivers a laser beam from an optical fiber through a slit lamp to a patient's retina, are known as "parfocal" and "defocus" systems. A parfocal system includes optics for focusing a sharp image of the fiber core (i.e., the fiber near field) to a spot (having size selectable from a range of spot sizes) on the patient's retina. The beam projected by a parfocal system through the eye (including the cornea) and onto the retina also includes fiber far field radiation, which has a Gaussian cross-section. The beam produced by a parfocal system has the disadvantage in that, when a large, sharped-edged fiber core image is focused on the retina, an undesirably high beam power density is often present at the cornea. This is because the beam divergence is low when the fiber core image size is large, giving a beam of nearly the same diameter through its entire transit of the eye (as illustrated in FIG. 11, to be discussed below).

The problem of small beam diameter and therefore high power density at the cornea typically exists when the sharp-edged fiber core image focused on the retina has large size. In some cases, depending on the type of fundus lens used during laser treatment, the corneal power density can exceed the power density at the retina with large, parfocal spot sizes.

An ophthalmic beam delivery system of the "defocus" type typically produces a beam whose waist is positioned behind the patient's retina. The image of the fiber core is also focused in a plane behind the patient's retina. Such a beam will have relatively low power density at the cornea, but undesirably has a Gaussian cross-section at the retina (due to the optical fiber far field radiation output characteristics).

The beam delivery system described in U.S. patent application Ser. No. 07/604,585, filed Oct. 26, 1990 (and assigned to the assignee of the present application) can be adjusted to operate either as a parfocal or a defocus system. However, it does not eliminate the above-described disadvantages of conventional parfocal and defocus systems.

Until the present invention, it was not known how to eliminate the described disadvantages and limitations of conventional ophthalmic beam delivery apparatus, of either the parfocal or defocus type.

SUMMARY OF THE INVENTION

The invention is an apparatus for delivering a defocused laser beam to a sharp-edged spot (having variable size) in a target plane. The defocused beam profile is such that the beam delivers low power to a plane of interest between the delivery apparatus and the target plane. In a preferred embodiment, the target plane is the retina of a patient's eye, and the defocused beam profile is controlled so that the beam delivers low power density to the eye's cornea.

The beam produced by the inventive apparatus is useful not only for ophthalmic surgery (in which laser photocoagulation is performed on the retina) but also for industrial laser heat treating and cutting applications in which a sharp-edged ("top hat") beam cross-section is needed at a target, particularly where delivery of low beam power densities at non-target structures are desirable.

In a preferred embodiment of the inventive apparatus, a laser beam emerges from an optical fiber, and a first lens (having short focal length) is mounted adjacent the optical fiber's output end to receive and transform the beam. A second lens (having short focal length) is mounted with variable position between the first lens and the target plane, for magnifying the image of the fiber core. Preferably, a lens system having long focal length (such as a pair of long focal length lenses) is mounted between the second lens and the target plane for relaying the magnified image of the fiber core to the target plane. By varying the position of the second lens, the characteristics of the beam delivered to the target plane can be controlled to fall into either of the following categories: parfocal (with small fiber core image and beam waist focused at the target plane, and relatively large Gaussian fiber far field image focused between the target plane and the delivery apparatus); and defocused (with a relatively large fiber core image focused at the target plane and a relatively small Gaussian fiber far field image focused beyond the target plane, which for large fiber core images in the target plane gives low power density at a plane of interest between the inventive delivery apparatus and the target plane).

BRIEF DESCRIPTION OF THE DRAWINGS

Each of FIGS. 5-8 is a diagram representing a beam profile produced by the FIG. 3 embodiment of the inventive apparatus.

DETAILED DESCRIPTION OF THE PREFERRED EMBODIMENT

The invention can be embodied in the retinal photocoagulator laser system 10 of FIG. 2. Laser system 10 includes laser means 12 for generating a beam of laser radiation having a wavelength and intensity suitable for the desired therapeutic procedure. The laser means 12 includes a suitable laser 14 and a laser control means 16. Laser control means 16 receives power from any suitable outside energy source and delivers it in a controlled fashion to laser 14. Lasers means suitable for ophthalmological therapies generally, and retinal therapies in particular, include Coherent Inc.'s laser consoles which provide both lasers and laser control means such as the Novus 2000, the Argon laser console model no. 920 A, the Argon-Krypton laser console model no. 920 A/K, and the dye laser console model no. 920 A/DYE.

Laser means 12 is coupled to laser focusing means 20 by laser transmission means 18. The laser transmission means is generally an optical fiber, although any suitable wave guide capable of efficient transmission of laser radiation at desired wavelengths would be suitable.

Laser focusing means 20 controls the spot size and focus mode of the laser radiation generated by laser means 12. Laser focusing means 20 may be comprised of any system of lenses, mirrors or other construction capable of focusing laser radiation. It is preferred to construct the laser focusing means 20 in the form of a lens system with an adjustable focal length that permits the spot size of the laser radiation at the target to be varied and which also permits the spot to be delivered in a parfocal or defocused mode for some desired range of spot sizes.

Optical means 24 for receiving and delivering laser radiation to the retina is coupled to the laser focusing means 20. In the embodiment shown in FIG. 2, optical means 24 includes a first mirror 26 for receiving laser radiation from the laser focusing means 20 and delivering it to the retina. The optical means 24 also includes a source 28 of visible light. Light generated by source 28 is received by mirrors 30 and 32 which reflect the visible light to the retina, thereby providing the illumination necessary for the physician to position the laser radiation.

Magnification means 40 positioned opposite the retina is employed to permit the physician to view the retina in order to position properly the laser radiation during therapeutic treatment. A suitable magnification means would be a microscope having magnifying capacity suitable for retinal enlargement. The combination of magnifying means 40 and optical means 24 is frequently referred to collectively as a "slit lamp" by those skilled in the art. Slit lamps suitable for use in the present invention include the Haag-Streit 900, the LDS 10a produced by Kowa, Inc. of Japan for Coherent Inc. and the Zeiss 30sL, produced by Carl Zeiss Co. of Germany.

In addition to the apparatus just described, a form of a contact lens 41 is typically positioned near the patient's eye to make it possible for the physician to focus an image of the retina. Normally the structure of the eye, in particular the action of the lens and cornea of the eye, interferes with the physician's ability to see an image which has been placed on the retina. Thus the physician uses one of a variety of lens systems designed to create an image at a point that is accessible to the microscope. The contact lens 41 is placed between the optical means 24 and the retina. Contact lens 41 is positioned so that it is in contact with the cornea through a gel which has been previously placed on the contact lens by the physician. Examples of typical contact lens systems used in conjunction with retinal photocoagulator laser systems include Goldmann 3 Mirror, Krieger, Panfundoscope and Mainster systems.

Turning now to FIG. 3, a version of laser focusing means 20 which embodies the invention will next be described. In FIG. 3, input laser beam 60 is introduced into focusing means 20 from the output end of optical fiber 50. Beam 60 propagates through short focal length lens L1 (fixedly mounted within focusing means 20 by mount means 63), and is transformed by lens L1 into transformed beam 62.

Figure 4:
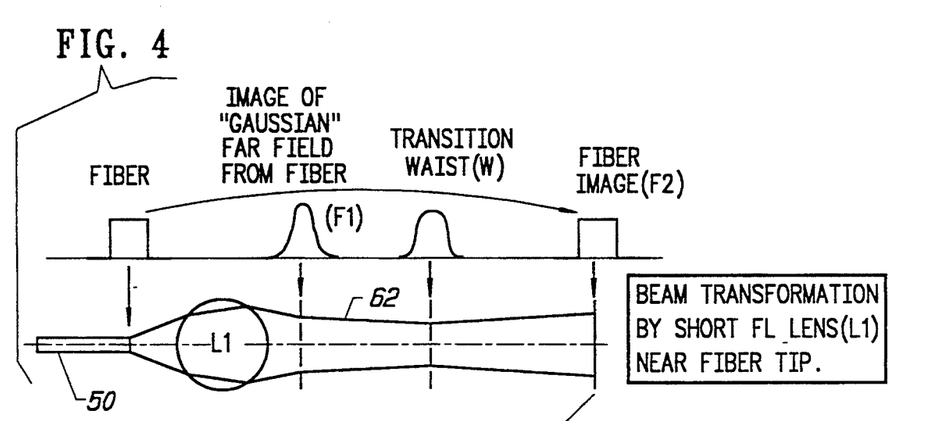
FIGS. 4 is a diagram representing the beam profile produced by positioning a single, short focal length lens adjacent an optical fiber.

The profile of beam 62 (in the absence of lenses L2, L3, and L4) is shown in FIG. 4. As indicated in both of FIGS. 3 and 4, an image of the fiber far field pattern (having a Gaussian cross-section) is created at plane F1 near lens L1. Lens L1 preferably has a sufficiently short focal length to cause the size of this image to be substantially the same as the desired spot size at the retina. Lens L1 should be positioned relative to fiber 50 so that an image of the fiber core (i.e., an image of the fiber near field having a top hat cross-section) is created at plane F2 (shown in FIG. 4) which has about same size as the image of the fiber far field at plane F1. With lens L1 so positioned, beam 62 has a waist at plane W (shown in FIGS. 3 and 4) between planes F1 and F2.

In the preferred embodiment shown in FIG. 3, short focal length lens L2 and long focal length collimating lens L3 are translatably mounted within means 20. Lens L2 is mounted on translatable mount means 64, and lens L3 is mounted on translatable mount means 65. Lens L2 functions as a magnifier of the fiber near field (fiber core) image. Long focal length lens L3 functions as a "collimator" of the fiber core image which has been magnified by lens L2. Fourth lens L4 (which has a long-focal length) forms a variable size image of the fiber core at the focal plane of lens L4. Thus, lenses L1, L2, L3, and L4 function together to produce a beam with a variable size fiber core image at the target plane, but whose waist progressively changes from a parfocal location for small fiber core images to a defocus location for large fiber core images.

Lenses L3 and L4 function as a relay lens system for relaying the magnified image of the fiber core to the target plane. Variations of the FIG. 3 apparatus can include alternative embodiments of such a relay lens system. Such variations can consist of one long focal length lens, or more than two long focal length lenses.

With reference to FIGS. 5-8, a detailed explanation will next be provided of the action of lenses L1 and L2 (of FIG. 3) in creating the progressive separation of the beam waist from the fiber core image as the fiber core image size is increased. Lenses L3 and L4 are omitted from FIGS. 5-8 for clarity. Lens L2 is shown in a different position relative to lens L1 in each of FIGS. 5, 6, 7, and 8.

If lens L2 is positioned in the plane F1 (a configuration shown in none of FIGS. 5-8), it will reduce (to a very small size) the fiber core image, but will not significantly affect the size of the (Gaussian) image of the fiber far field at plane F2 from the size the latter image has in the FIG. 4 configuration.

Figure 5:
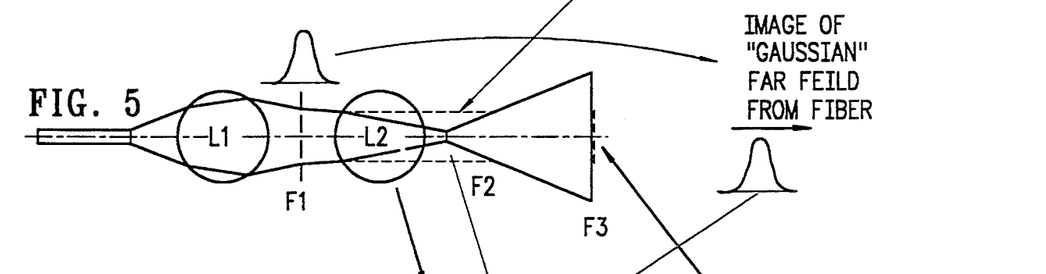

If lens L2 is moved away from plane F1 (about one focal length of L2 from F1 as shown in FIG. 5), it will focus a fiber core image in plane F2 that is slightly larger than if lens L2 were positioned in plane F1. It will also focus the fiber far field radiation to a large Gaussian far field image in plane F3 at a great distance from L2. The far field image will have larger cross-section (in plane F3) than the fiber core image in plane F2. The beam waist will occur at substantially the same location as the fiber core image.

Figure 6:
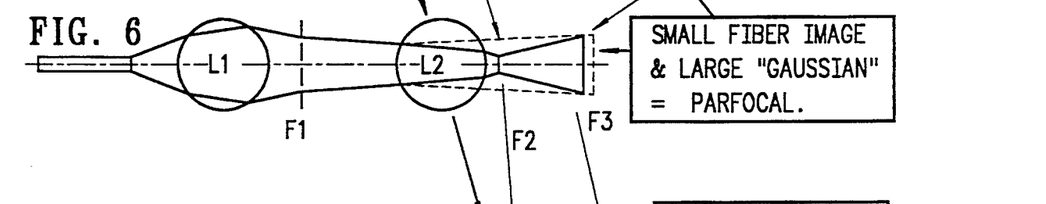

If lens L2 is moved farther (i.e., more than one focal length of lens L2) away from plane F1 to the position shown in FIG. 6, the size of the fiber core image (in plane F2) will increase, the size of the far field image will decrease, plane F3 (the plane of the far field image) will move closer to L2, and the beam waist will move a negligible distance from plane F2 toward plane F3.

Figure 7:
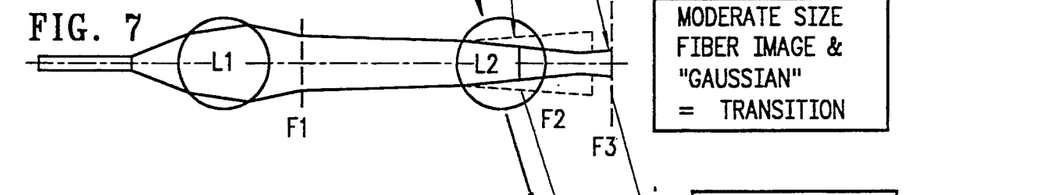

If lens L2 is moved even farther away from plane F1 to the position shown in FIG. 7, the fiber core image size focused in plane F2 will again increase, the far field image size will decrease, and the far field image plane (F3) will move toward L2. This results in both images having about the same size, and causes the beam waist to move to a location about midway between F2 and F3. The FIG. 7 configuration thus delivers a defocused beam to plane F2, but this beam has qualitatively different characteristics than defocused beams delivered by conventional ophthalmic beam delivery systems of the "defocus" type. The beam cross-section at F2 is substantially sharper (i.e., has more sharply defined edges) than that produced by a conventional defocus type delivery system.

Figure 8:
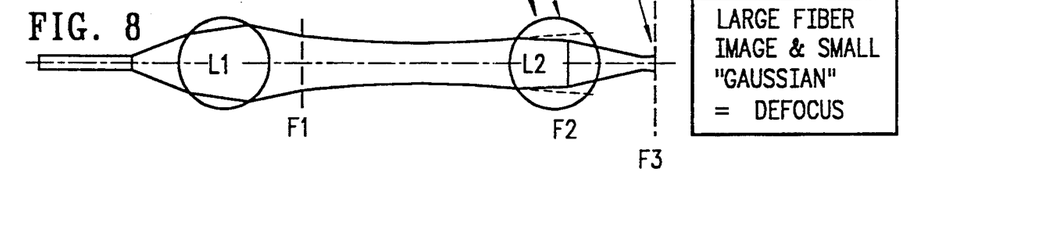

If lens L2 is moved even farther away from plane F1 to the position shown in FIG. 8, the fiber core image size focused in plane F2 will become larger while the far field image size (in plane F3) shrinks, and the far field image plane (F3) moves toward L2. This results in the beam waist moving close to plane F3 where a small image of the fiber far field is located. The FIG. 8 configuration thus delivers a defocused beam to plane F2 having qualitatively different characteristics than defocused beams delivered by conventional ophthalmic beam delivery systems of the "defocus" type. The beam has a top hat cross-section in plane F2 (with sharply defined edges as in FIG. 1).

Positions of lens L2 between that in FIG. 7 and that in FIG. 8, can produce more than enough magnification of the fiber core image to give a useful range of sharp-edged spot sizes in target plane F2.

To complete the description, the effect of lenses L3 and L4 on the configurations of FIGS. 5-8 will next be discussed. In operation of the inventive apparatus, lens L3 is moved to follow the location of the fiber core image (at plane F2), so that lens L3 is maintained at a distance of one focal length from the fiber core image. This results in maintenance of a collimated image of the fiber core beyond lens L3 in the configuration of each of FIGS. 5-8. Fixed lens L4 forms a variable size image of the fiber core (depending on the configuration of lenses L2 and L3) at a fixed distance of one focal length from L4 (i.e., at plane F4 shown in FIG. 12).

The configuration shown in FIG. 5 gives a small fiber core image located at the beam waist, with a large convergence angle. When the fiber image is located at the patient's retina, a small spot with a sharp edged beam cross-section is produced, and the beam size at the cornea is large giving a low power density. As lenses L2 and L3 are moved to the FIG. 6 configuration, the fiber image grows, the beam convergence is reduced, and the beam waist shifts only a negligible amount from the fiber core image location. The resulting beam still produces a reasonably small spot with a sharp edged beam cross-section at the retina, while the beam size at the cornea is reduced (but still large) giving a low power density.

Figure 9:
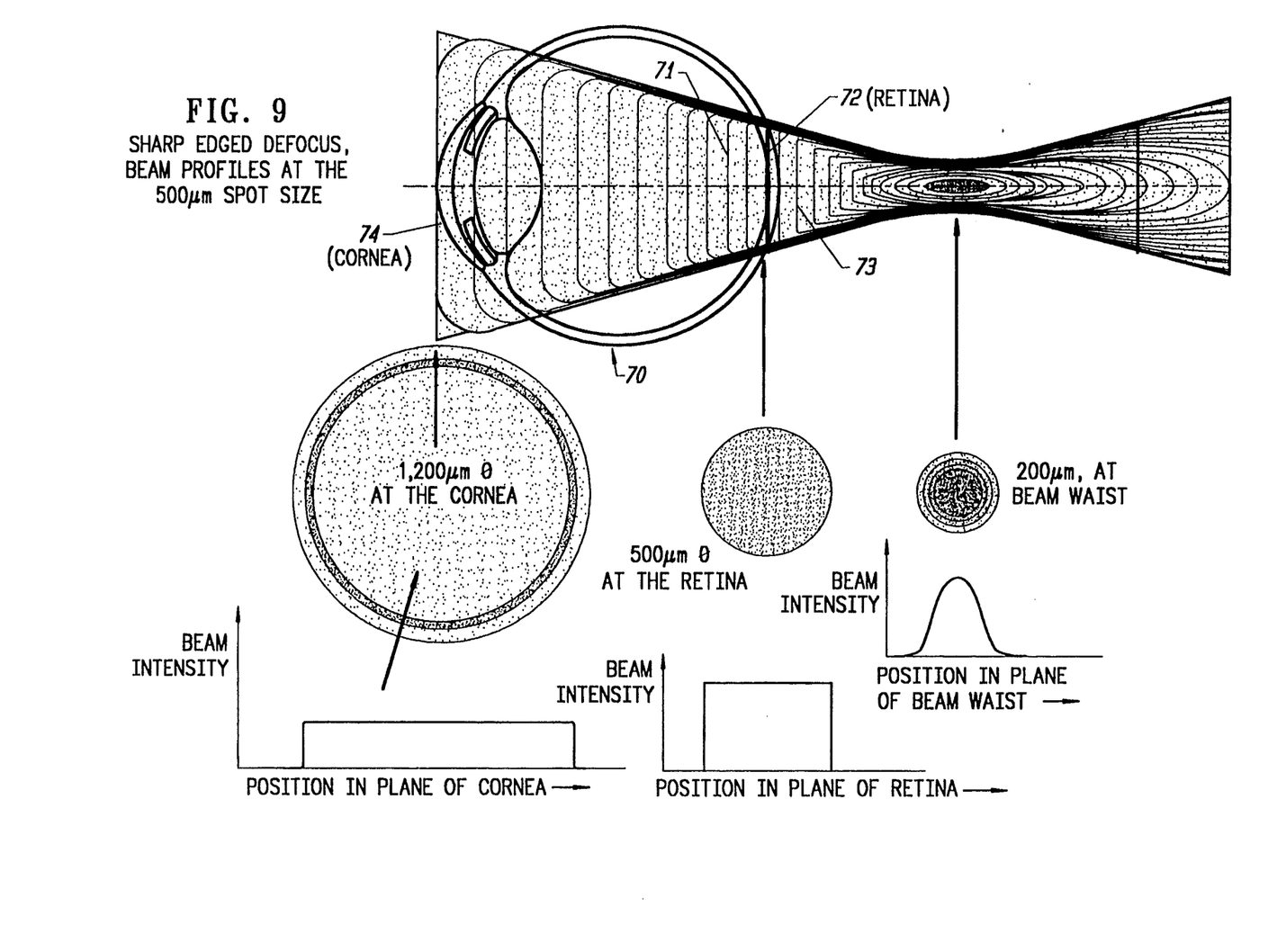
FIG. 9 is a diagram representing the profile of a beam delivered to a patient's eye by an embodiment of the invention, and three different cross-sectional views of the beam, and three graphs of beam intensity in different cross-sectional planes along the beam profile.
Figure 10:
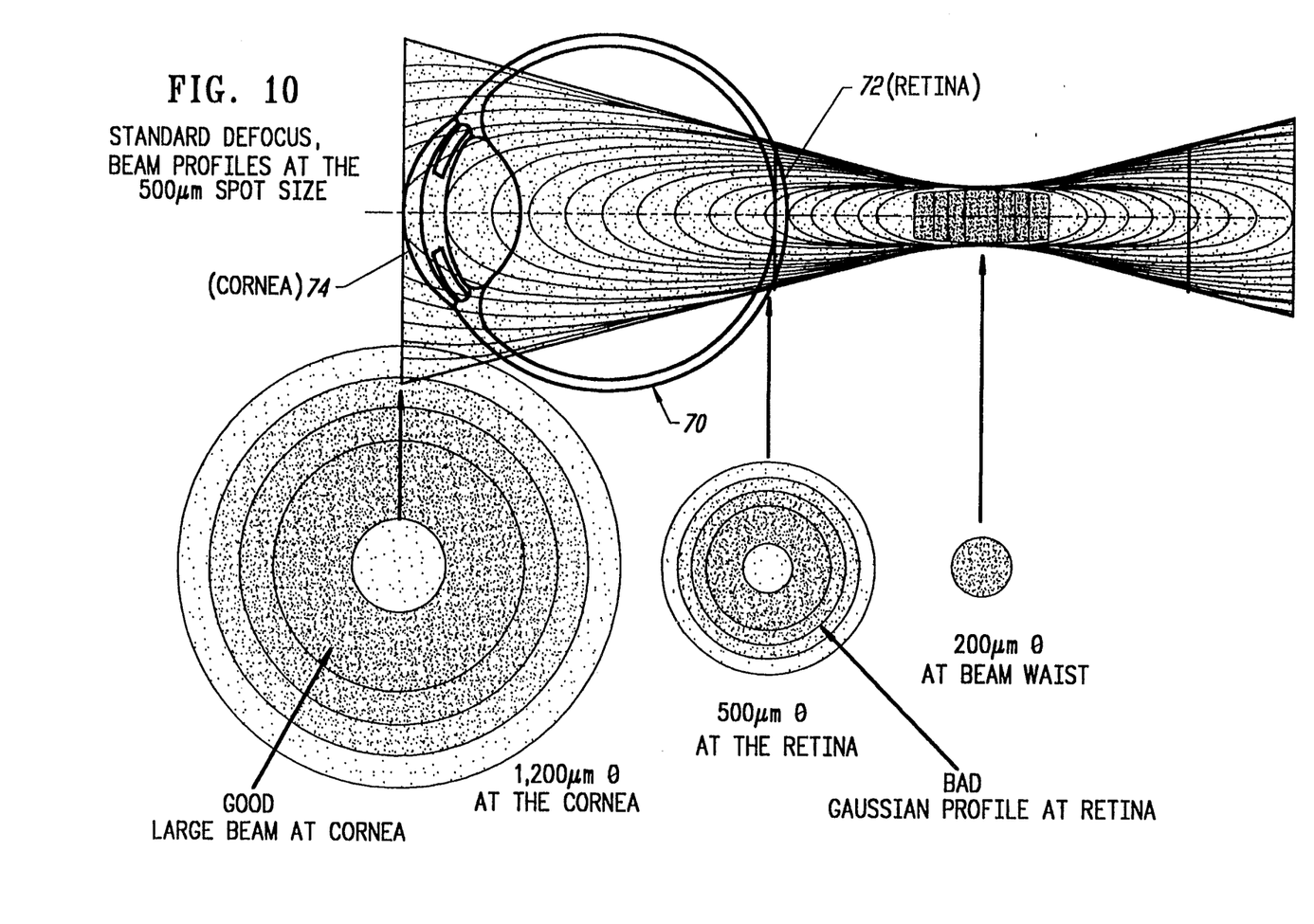
FIG. 10 is a diagram representing the profile of a beam delivered to a patient's eye by a conventional defocused beam apparatus, and three different cross-sectional views of the beam in different cross-sectional planes along the beam profile.

The beams produced by the configurations of FIGS. 5 and 6 are truly parfocal and equivalent to those of a conventional parfocal delivery system. However, as lenses L2 and L3 continue to move away from lens L1 to the configurations of FIGS. 7 and 8, the system smoothly and progressively changes into a new type of "defocus" system, that continually maintains sharp edged beam cross-sections at the retina and large beam diameters at the cornea (as shown in FIG. 9). This is in contrast to conventional defocus systems that produce a large beam diameter at the cornea and a "Gaussian" cross-section at the retina (as shown in FIG. 10). It is also in contrast with conventional parfocal systems that produce a small beam diameter at the cornea and a sharp-edged beam cross-section at the retina (as shown in FIG. 11).

Moving lenses L2 and L3 to the FIG. 7 configuration produces more growth in the fiber core image size, a small shift of the beam waist away from the fiber core image, and a smaller reduction in the beam convergence. The beam produces a moderately sized spot on the retina having a sharp-edged cross-section, and a moderately sized spot on the cornea (for a low power density).

As lenses L2 and L3 are moved to the FIG. 8 configuration, the fiber core image size continues to grow, and the beam waist moves farther away from the fiber core image, but the beam convergence is almost unchanged (in relation to the beam convergence in the FIG. 7 configuration). The beam produces a large sized spot (having diameter of 500 microns, or larger, in some embodiments of the invention) on the retina with a sharp edged cross-section, while maintaining the moderately sized spot size on the cornea (larger than 1 mm) for low power density.

Figure 12:
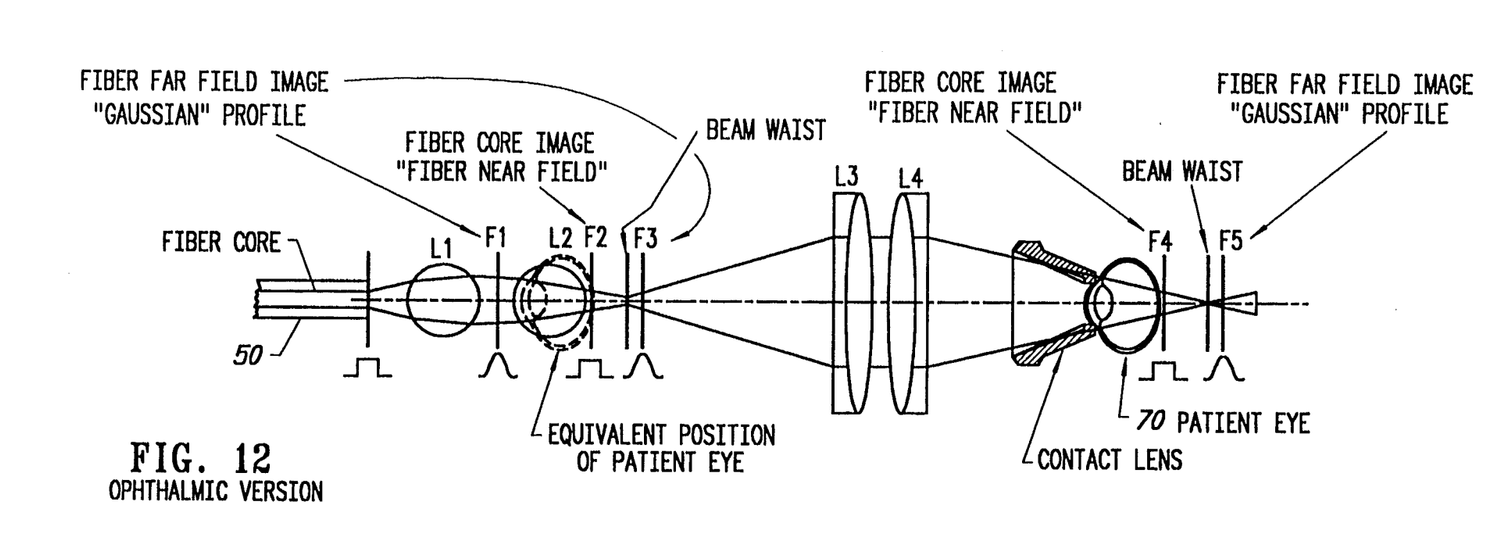
FIG. 12 is a diagram representing the profile of a beam delivered to a patient's eye by a first preferred embodiment of the invention.

The full beam profile produced by lenses L1, L2, L3, and L4 in the FIG. 8 configuration is shown in FIG. 12, with a conventional contact lens positioned (as shown in FIG. 12) immediately in front of the patient's eye 70.

In the FIG. 8 configuration (and configurations in which lens L2 is positioned between the positions shown in FIGS. 7 and 8), the invention delivers a useful, sharp-edged fiber core image over a large depth of field in a "defocused" portion of the beam. The invention also shifts the portion of the beam having Gaussian cross-section to a position near the beam waist (and away from the target plane). FIG. 9 illustrates these features of the inventive apparatus.

FIG. 9 represents the profile of a beam delivered to patient's eye 70 by an embodiment of the invention having configuration as shown in FIG. 8, and designed for delivering a 500 micron diameter, sharp-edged spot to the retina. At cornea 74 of eye 70, the beam cross-section (in a plane perpendicular to FIG. 9) has a large diameter (1200 microns) and thus a low power density. The beam cross-section at cornea 74 is substantially sharp-edged.

The beam is focused at retina 72 to a sharp-edged (top hat) fiber core image having a cross-section of 500 microns. This sharp-edged fiber core image has a large depth of field. Thus, for example, a sharp-edged image having size only slightly larger than 500 microns is delivered at plane 71, and a sharp-edged image having size only slightly smaller than 500 microns is delivered at plane 73, on either side of retina 72.

The beam waist has a Gaussian cross-section of diameter 200 microns, and occurs beyond retina 72 (to the right of retina 72 in FIG. 9).

In general, by varying the positions of L2 (the second short focal length lens) and lens L3 in the above-described embodiment of the invention, the characteristics of the beam delivered to the target plane can be controlled to fall into either of the following categories: parfocal (with small fiber core image focused in the target plane; and "defocused" (with a relatively large, sharped-edged fiber core image at the target plane and a relatively small Gaussian fiber far field image focused beyond the target plane, which for large fiber core images in the target plane gives low power density at a plane of interest between the inventive apparatus and the target plane). The sharp-edged, defocused beam produced by the above-described embodiment of the invention is particularly useful for ophthalmic surgical applications.

It should be appreciated that FIGS. 9-11 are not drawn to scale, in the sense that in these Figures, the beam diameters are exaggerated relative to the eye diameter. If FIGS. 9-11 were redrawn to scale, the beam diameters would be so much smaller relative to the eye diameter, that it would be impossible to discern the details discussed in this specification regarding the beam profiles and cross-sections.

Another embodiment of the invention, to be described with reference to FIG. 13, produces a type of sharp-edged, defocused beam that is better suited for performing non-ophthalmic surgery than for performing ophthalmic surgery. The FIG. 13 apparatus is identical to the apparatus described above with reference to FIG. 12, except that short focal length lens L2 is omitted. In both the FIG. 12 and FIG. 13 apparatus, long focal length lenses L3 and L4 relay the image of the fiber core to the target plane.

Figure 13:
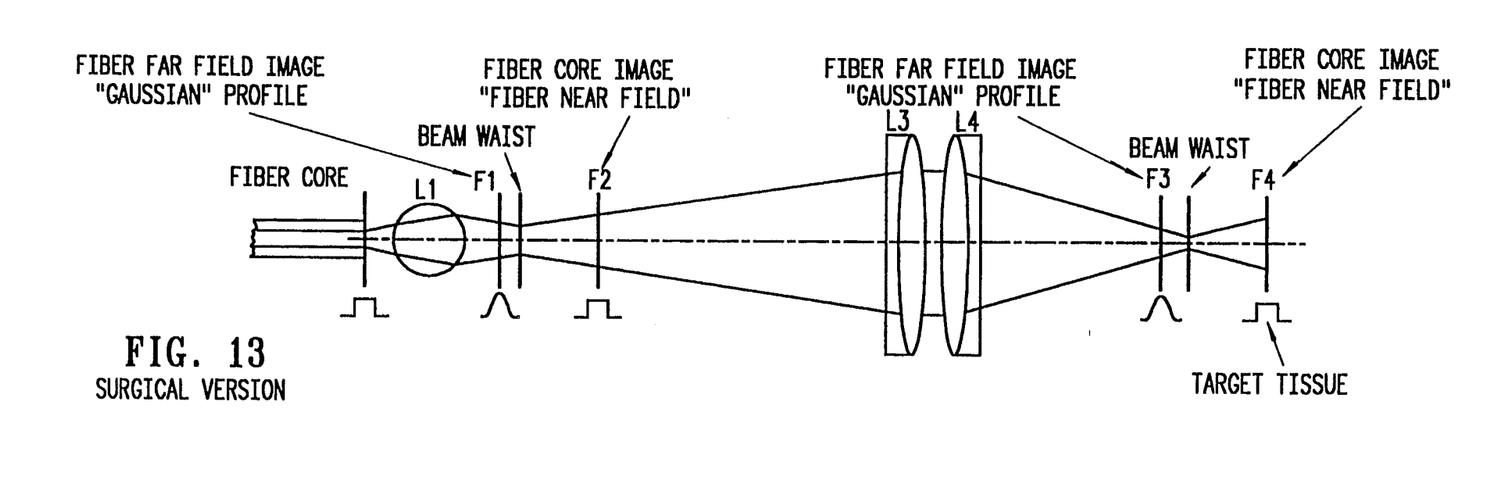
FIG. 13 is a diagram representing the profile of a beam delivered to a patient's eye by a second preferred embodiment of the invention.

Like the FIG. 12 apparatus, the FIG. 13 apparatus delivers a beam having a sharp-edged cross-section to the target plane (F4), with the beam's waist located away from the target plane. However, in the beam profile of FIG. 13 differs from that of FIG. 12, in the following respect. In FIG. 13, lenses L3 and L4 relay the beam waist to a location between lens L4 and the target plane, and relay the Gaussian far field image to a plane (F3) between the beam waist and lens L4. In FIG. 12, lenses L3 and L4 relay the beam waist to a location beyond the target plane, and relay the Gaussian far field image to a plane (F5) beyond the beam waist. Thus, in the case that the target plane coincides with a patient's retina, the waist of the beam produced the FIG. 13 apparatus may undesirably fall within the patient's eye (between the retina and lens L4), rather than beyond the patient's eye as in FIG. 12.

Various modifications and alterations in the structure and method of operation of this invention will be apparent to those skilled in the art without departing from the scope and spirit of this invention. Although the invention has been described in connection with specific preferred embodiments, it should be understood that the invention as claimed should not be unduly limited to such specific embodiments.

What is claimed is:

1. An optical system for delivering a laser beam from an exit plane to a target plane, wherein the beam in the exit plane has a sharp edge intensity profile, said system comprising:

first focusing means for transforming the beam and creating a magnified image of the exit plane and a transformed beam waist;

second focusing means for relaying the transformed beam such that the image of the exit plane coincides with the target plane; and means for adjusting the focus of at least one of said focusing means in a manner to vary the position of the relayed transformed beam waist while maintaining the image of the exit plane in the target plane thereby preserving a sharp edge intensity profile in the target plane as the diameter of the beam in the target plane is varied.

2. An optical system as recited in claim 1 wherein target plane is located between the second focusing means and the relayed transformed beam waist.

3. An optical system as recited in claim 1 wherein the relayed transformed beam waist is located between the second focusing means and the target plane.

4. An optical system as recited in claim 1 wherein the exit plane is defined by an output end of an optical fiber.

5. An optical system as recited in claim 1 wherein said first focusing means includes at least one lens means the position of which can be varied to vary the diameter of the image of the exit plane.

6. An optical system as recited in claim 5 wherein said second focusing means includes a first lens means for collimating the transformed beam and a second lens means for focusing the image of the exit plane to the target plane.

7. An ophthalmic laser system for treating the retina comprising:

means for generating a laser beam;

an optical fiber having an input end for receiving the laser beam and a delivery end out of which the beam is emitted, with the beam emitted at the delivery end having a sharp edge intensity profile;

first lens means for transforming the beam exiting the delivery end of the fiber and creating a magnified image of the delivery end of the fiber and a transformed beam waist;

second lens means for relaying the transformed beam such that the image at the delivery end of the fiber coincides with the plane of the retina; and means for adjusting the focus of at least one of said lens means in a manner to vary the position of the relayed transformed beam waist behind the retina while maintaining the image of the delivery end of the fiber in the plane of the retina thereby preserving a sharp edge intensity profile in the retinal plane as the diameter of the beam in the retinal plane is varied.

8. An optical system as recited in claim 7 wherein said first focusing means includes at least one lens means the position of which can be varied to vary the diameter of the image of the delivery end of the fiber.

9. An optical system as recited in claim 8 wherein said second focusing means includes a first lens means for collimating the transformed beam and a second lens means for focusing the image of the delivery end to the retinal plane.

10. An optical system for delivering a laser beam from an exit plane to a target plane, wherein the beam in the exit plane has a sharp edge intensity profile, said system comprising:

first focusing means located between the exit plane and the target plane for transforming the beam and creating an image of the exit plane which is spatially separated from the waist of the transformed beam; and second focusing means for relaying an image of the transformed beam including the image of the exit plane and the spatially separated waist and wherein the location of the relayed image of the exit plane is selected so that the target plane lies within the depth of focus of the image of the exit plane and wherein the location of the relayed waist of the transformed beam is selected to be spaced from the target plane so that the beam in the target plane has a sharp edge intensity profile and a diameter larger than the diameter of the relayed beam waist.

11. An optical system as recited in claim 10 further including a means for adjusting the position of the relayed waist to vary the diameter of the beam in the target plane.

12. A system as recited in claim 10 further including a means for adjusting the focus of said first focusing means to vary the diameter of the image of the exit plane as well as the spacing between the image and the relayed transformed beam waist.

13. A system as recited in claim 12 further including a means for adjusting the focus of the second focusing means to maintain the image of the exit plane in the target plane as the diameter of the beam in the target plane is varied.

* * * * *